United States Patent
Davids et al.

(10) Patent No.: US 12,268,508 B2
(45) Date of Patent: Apr. 8, 2025

(54) SYSTEM FOR AND METHOD OF RAPID PERIPHERAL NERVE STIMULATION ASSESSMENT OF GRADIENT COILS

(71) Applicant: The General Hospital Corporation, Boston, MA (US)

(72) Inventors: Mathias Davids, Cambridge, MA (US); Lawrence L. Wald, Cambridge, MA (US); Bastien Guerin, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1016 days.

(21) Appl. No.: 17/118,155

(22) Filed: Dec. 10, 2020

(65) Prior Publication Data
US 2021/0186405 A1   Jun. 24, 2021

Related U.S. Application Data

(60) Provisional application No. 62/946,227, filed on Dec. 10, 2019.

(51) Int. Cl.
*A61B 5/311* (2021.01)
*A61B 5/0515* (2021.01)
*A61B 5/388* (2021.01)
*G01R 33/00* (2006.01)

(52) U.S. Cl.
CPC ............ *A61B 5/311* (2021.01); *A61B 5/0515* (2013.01); *A61B 5/388* (2021.01); *G01R 33/0029* (2013.01); *A61B 2560/04* (2013.01)

(58) Field of Classification Search
CPC ....... A61B 5/311; A61B 5/0515; A61B 5/388; A61B 2560/04; A61B 5/055; G01R 33/385; G01R 33/288
See application file for complete search history.

(56) References Cited

U.S. PATENT DOCUMENTS

| | | | | |
|---|---|---|---|---|
| 2010/0308829 | A1* | 12/2010 | Vu | H03K 6/04 327/291 |
| 2011/0152665 | A1* | 6/2011 | Lai | G01R 33/288 600/410 |
| 2018/0133467 | A1* | 5/2018 | Wald | A61N 1/086 |

(Continued)

OTHER PUBLICATIONS

Guerin et al., The ultimate signal-to-noise ratio in realistic body models, Magnetic Resonance in Medicine, vol. 78, iss 5, Nov. 2017, pp. 1969-1980 (Year: 2017).*

(Continued)

*Primary Examiner* — Jacqueline Cheng
*Assistant Examiner* — Tho Q Tran
(74) *Attorney, Agent, or Firm* — QUARLES & BRADY LLP (57) ABSTRACT

A method for assessing peripheral nerve stimulation (PNS) for a coil geometry includes retrieving a PNS Huygens' P-matrix for a body model. The PNS Huygens' P-matrix is defined on a Huygens' surface enclosing the body model. The method further includes generating a coil specific PNS P-matrix for the coil geometry based on at least the PNS Huygens' P-matrix for the body model, determining at least one PNS threshold for the coil geometry based on the coil specific PNS P-matrix, and storing the at least one PNS threshold in a storage device.

20 Claims, 7 Drawing Sheets

(56) References Cited

U.S. PATENT DOCUMENTS

| | | | | |
|---|---|---|---|---|
| 2018/0231624 A1* | 8/2018 | Panther | ............... | G01R 33/307 |
| 2020/0057124 A1* | 2/2020 | Harris | ............... | G01R 33/288 |
| 2022/0221541 A1* | 7/2022 | vom Endt | ............ | G01R 33/543 |
| 2023/0088438 A1* | 3/2023 | Schneider | ............ | G01R 33/543 |

OTHER PUBLICATIONS

Feng et al., A Technique to Evaluate MRI-Induced Electric Fields at the Ends of Practical Implanted Lead, IEEE Transactions on Microwave Theory and Techniques, vol. 63, No. 1, pp. 305-313, Jan. 2015 (Year: 2015).*

Feng et al., Efficient evaluation of MRI-induced electric fields in the vicinity of implantable lead, 2013 Texas Symposium on Wireless and Microwave Circuits and Systems (WMCS), Waco, TX, USA, 2013, pp. 1-4 (Year: 2013).*

Li et al., "An Improved Hybrid MoM/FDTD Technique for MRI RF Coils Modeling Using Huygen's Equivalent Surface Method," 2007 29th Annual International Conference of the IEEE Engineering in Medicine and Biology Society, 2007, pp. 3898-3901 (Year: 2007).*

Lemdiasov et al., "A stream function method for gradient coil design," Concepts Magn Reson, vol. 26B, No. 1, pp. 67-80, Aug. 2005.

Davids et al., "Predicting magnetostimulation thresholds in the peripheral nervous system using realistic body models," Sci Rep, vol. 7, No. 1, p. 5316, 2017.

Klein et al., "Sensitivity analysis of neurodynamic and electromagnetic simulation parameters for robust prediction of peripheral nerve stimulation," Phys Med Biol, 2018.

Davids et al., "Simulation of peripheral nerve stimulation thresholds of MRI gradient coils," Proceedings of the 26th Annual Meeting of ISMRM, Paris, France, 2018.

Davids et al., "The PNS oracle: a modified neural activation function metric for rapid assessment of peripheral nerve stimulation (PNS)," Proceedings of the 27th Annual Meeting of ISMRM, Montreal, Canada, 2019.

Davids et al., "Peripheral Nerve Stimulation (PNS) constrained gradient coil design within a Boundary Element Method Stream Function (BEM-SF) optimization", ISMRM 2019.

Davids et al., "Prediction of peripheral nerve stimulation thresholds of MRI gradient coils using coupled electromagnetic and neurodynamic simulations," Magn Reson Med, vol. 81, No. 1, pp. 686-701, 2019.

* cited by examiner

SYSTEM FOR AND METHOD OF RAPID PERIPHERAL NERVE STIMULATION ASSESSMENT OF GRADIENT COILS

CROSS-REFERENCE TO RELATED APPLICATIONS

This application is based on, claims priority to, and incorporates herein by reference in its entirety U.S. Ser. No. 62/946,227 filed Dec. 10, 2019, and entitled "System for and Method of Rapid Peripheral Nerve Stimulation Assessment of 2D or 3D Gradient Coil Windings."

STATEMENT REGARDING FEDERALLY SPONSORED RESEARCH

This technology was made with government support under grants R00EB019482, U01EB025121 and U01EB025162 awarded by the National Institutes of Health. The government has certain rights in the technology.

FIELD

The present disclosure relates generally to assessing peripheral nerve stimulation (PNS) of a gradient coil and, in particular to a system and method for rapid assessment of PNS of a gradient coil based on a PNS predictor defined on a Huygens' surface of a body model.

BACKGROUND

The ability to quickly assess Peripheral Nerve Stimulation (PNS) is becoming increasingly important for optimizing stimulation devices, as well as devices for which PNS is an unwanted side effect such as gradient coils in Magnetic Resonance Imaging (MM) or drive coils in Magnetic Particle Imaging (VIPI). In both cases, the device operator or designer must quickly assess if and where a candidate electrode or coil design induces action potentials (APs) in the body. Any insights into the device's PNS locations within the body and the onset PNS thresholds (i.e., the smallest stimulating electrode voltage or coil current amplitude inducing an action potential) can allow the device designer or operator to iteratively modify the device or change its position relative to the body to either increase or decrease the strength of the stimulation.

One process developed for PNS assessment of MRI gradient coils (e.g., estimating PNS thresholds) includes simulations of the titration process that incorporates a full neurodynamic model of the nerves in the body. The full neurodynamic model is a mathematical model of various ion population concentrations in the nerve cell and is coupled to an electromagnetic model of the human body to predict PNS. Specifically, this PNS simulation workflow starts with simulating the electric fields that an external coil induces in a body model. The electric fields are then projected onto the nerve fiber trajectories included in a nerve atlas of the body model (e.g., a detailed nerve atlas of the nerve fibers in the human body co-registered to the body model) and the projected electric fields are integrated to obtain the electric potential variations along the nerves (this is the driving function of PNS and the input to the neurodynamic model). Finally, this potential variation is fed into the neurodynamic model to predict the nerve's response. The output of the model is the intracellular potential changes along the nerve over the time-course of the applied coil current that may show induced action potentials if the nerve was stimulated.

Although this process (i.e., a full electromagnetic plus neurodynamic model framework) is very useful when analyzing candidate coil designs during the design phase, it is not straightforward to incorporate it in the standard approach for numeric gradient winding optimization. The PNS metric from this PNS prediction process cannot be readily used as a linear constraint in a numeric optimization framework due to the non-linearity of the neurodynamic model. In addition, the electromagnetic and neurodynamic simulations are very time-consuming (both of which can take multiple hours up to several days), which does not permit the PNS metric to be computed repeatedly during a numerical optimization.

In order to convert the PNS metric to a form that is better suited to numerical optimization, a rapid linear PNS predictor or "oracle" was developed that can be used in gradient coil design optimization and is a surrogate for the full neurodynamic model. Accordingly, a PNS oracle allows the estimation or prediction of PNS thresholds without the need to simulate the complex neurodynamics of the nerve fibers using full neurodynamic modeling. The PNS oracle can estimate the PNS threshold of a nerve segment from the electric field using only linear operations (projection of the electric field onto the nerve to obtain the potential changes, finite differencing, convolution, and scaling). The PNS oracle assigns a value to every section of a nerve that inversely scales with the PNS threshold. The fact that the PNS oracle is linear in the electric field (and thus linear in the current fed to the coil that induces these E-fields) allows precomputing the PNS oracle for a large number of coil or wire pieces. The precomputed PNS oracle(s) may then be used to quickly assess arbitrary coil/wire configurations. The determination of PNS thresholds for the arbitrary coil/wire configurations using the pre-computed PNS oracle is very fast (milliseconds), rendering it adequate for numerical optimization that requires repeated evaluation of hundreds of PNS responses. In addition, the PNS oracle can be directly incorporated in the standard approach for the design of MRI gradient coils, namely the boundary element method stream function (BEM-SF) approach. In the BEM-SF approach, the PNS oracle can be pre-computed for each stream function basis. This precomputation step involves simulating the electric field (E-field) induced by a stream function basis. The E-field is then projected onto the nerve fiber path and integrated to obtain the electric potential changes. The PNS oracle can then be directly calculated from the electric potential changes. Combining PNS oracle contributions induced by all stream function basis in all nerve segments yields a so-called P-matrix that can be incorporated in the BEM-SF winding optimization as a linear PNS penalty matrix to enforce PNS-optimized coil layouts. However, the PNS oracle approach still requires the simulation of electric fields in the body model (from which the PNS oracles can be computed). In fact, to obtain the full P-matrix, the electric fields need to be simulated for every stream function basis individually to extract their PNS oracles. This process can take more than a week for a single gradient coil design shape. In addition, every modification of the coil former shape requires the re-computation of the P-matrix.

SUMMARY

In accordance with an embodiment, a method for assessing peripheral nerve stimulation (PNS) for a coil geometry includes retrieving a PNS Huygens' P-matrix for a body model. The PNS Huygens' P-matrix is defined on a Huygens' surface enclosing the body model. The method further includes generating a coil specific PNS P-matrix for the coil geometry based on at least the PNS Huygens' P-matrix for the body model, determining at least one PNS threshold for the coil geometry based on the coil specific PNS P-matrix, and storing the at least one PNS threshold in a storage device.

In accordance with another embodiment, a magnetic resonance imaging (MRI) system includes a magnet system configured to generate a polarizing magnetic field about at least a portion of a subject, a magnetic gradient system including a plurality of gradient coils configured to apply at least one gradient field to the polarizing magnetic field and a radio frequency (RF) system configured to apply an excitation field to the subject and to receive MR data from the subject using a coil array. The MRI system further includes a computer system that is programmed to retrieve a PNS Huygens' P-matrix for a body model. The PNS Huygens' P-matrix is defined on a Huygens' surface enclosing the body model. The computer system is further programmed to generate a coil specific PNS P-matrix for a predetermined gradient coil geometry based on at least the PNS Huygens' P-matrix for the body model, determine at least one PNS threshold for the gradient coil geometry based on the coil specific PNS P-matrix, and store the at least one PNS threshold in a storage device.

In accordance with another embodiment, a method for optimizing a design of a gradient coil geometry includes creating a current density distribution of the gradient coil geometry, determining the B-field generated by each stream function basis associated with the current density distribution and determining a coil specific PNS P-matrix for the gradient coil geometry based on at least a PNS Huygens' P-matrix for a body model. The PNS Huygens' P-matrix is defined on a Huygens' surface enclosing the body model. The method further includes determining a current density pattern using an optimization process including the coil specific PNS P-matrix for the gradient coil geometry, and storing the current density pattern.

BRIEF DESCRIPTION OF THE DRAWINGS

The present disclosure will hereafter be described with reference to the accompanying drawings, wherein like reference numerals denote like elements.

DETAILED DESCRIPTION

The present disclosure describes systems and methods for assessing peripheral nerve stimulation of a gradient coil or magneto-stimulation (or magnetic stimulator) device using a coil specific PNS predictor that is generated using a linear PNS penalty matrix (P-matrix) defined on a Huygens' surface of a body model (hereinafter referred to as a PNS Huygens' P-matrix ($P_H$)). The coil specific PNS predictor is also in the form of a linear PNS penalty matrix, is generated for a specific coil geometry (e.g., a coil winding pattern or a coil former shape) and is hereinafter referred to as a coil specific PNS P-matrix ($P_D$). The PNS Huygens' P-matrix can be pre-computed and stored and, therefore, only needs to be generated once for each body model. For assessment of a specific gradient coil geometry (e.g., winding pattern, coil former shape), the PNS Huygens' P-matrix may be translated to a coil specific PNS P-matrix associated with the coil geometry using a mapping matrix or a mapping vector. Accordingly, the PNS Huygens' P-matrix may be mapped to individual coil shapes and winding patterns. The generation of the coil specific PNS P-matrices does not require the computation of electric fields and PNS predictor values for each different coil former shape or coil winding. A coil specific PNS P-matrix may be directly incorporated into a standard gradient winding optimization approach for gradient design, such as the boundary element method stream function (BEM-SF) approach. A coil specific PNS P-matrix may also be used to rapidly assess PNS (e.g., predict PNS thresholds) for discrete coil windings (e.g., existing or hypothetical gradient coils). In addition, coil specific PNS P-matrix may be used to rapidly assess PNS (e.g., predict PNS thresholds) for a magneto-stimulation (or magnetic stimulator) device, for example, consisting of an array of magnetic coils, that may be used for therapy and treatment applications. The system and methods for assessing PNS of gradient coils or magneto-stimulation devices may be used, for example, to design PNS optimized gradient coils, for online PNS monitoring on an MR Scanner for different patient positions and guided placement of magneto-stimulation devices (coil or coil array).

Figure 1:
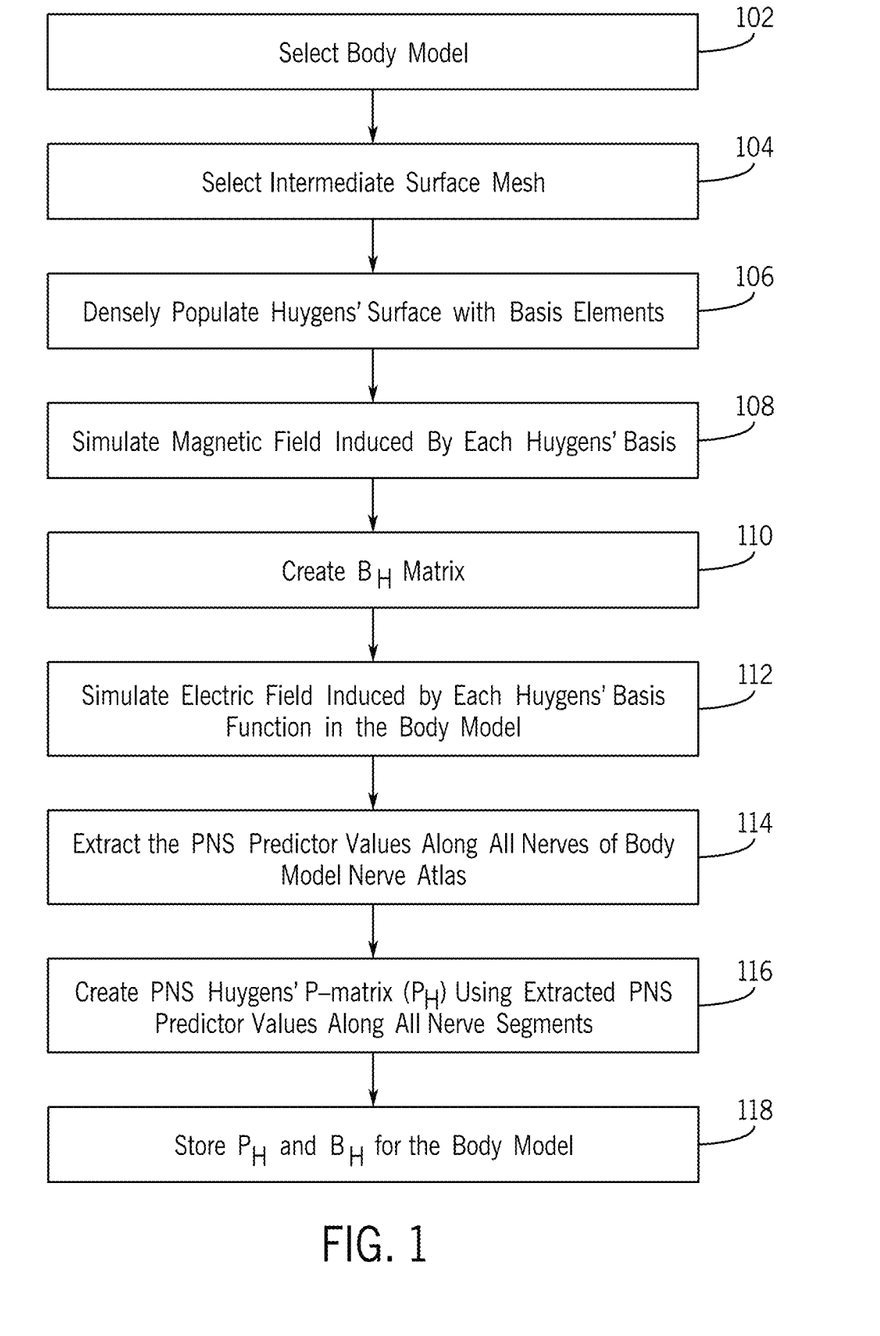
FIG. 1 illustrates a method for generating a PNS Huygens' P-matrix for assessment of peripheral nerve stimulation in accordance with an embodiment.
Figure 2:
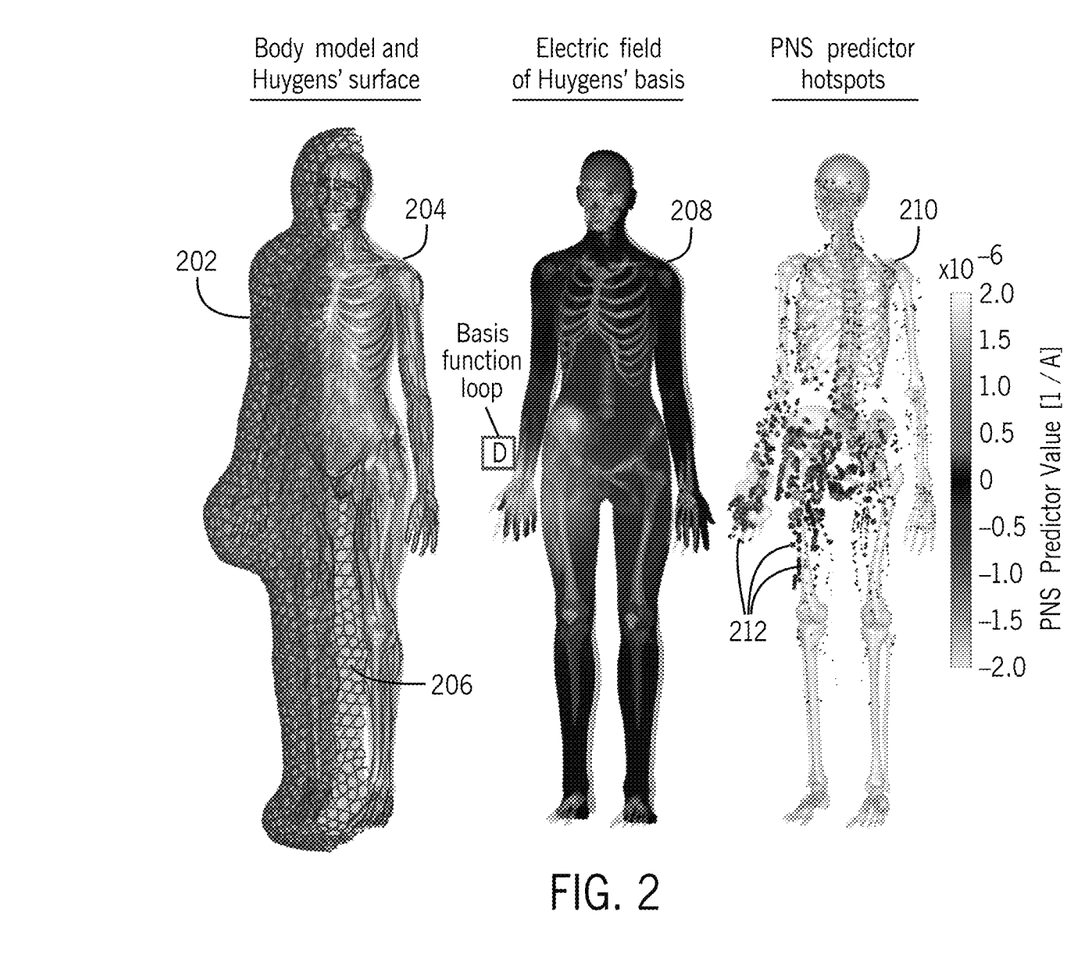
FIG. 2 illustrates various steps of the method of FIG. 1 for generating a PNS Huygens' P-matrix in accordance with an embodiment.

FIG. 1 illustrates a method for generating a PNS Huygens' P-matrix for assessment of peripheral nerve stimulation in accordance with an embodiment and FIG. 2 illustrates various steps of the method of FIG. 1 for generating a PNS Huygens' P-matrix in accordance with an embodiment. Referring to FIGS. 1 and 2, a body model 204 is selected at block 102. In one embodiment, the body model 204 may be selected by a user via a user input of a computer system. At block 104, an intermediate surface mesh (i.e., the Huygens' surface) 202 is chosen so that the entire body model is enclosed with a minimum distance between the Huygens' surface and the boundary of the body model (e.g., 5 cm) and the Huygens' surface 202 is closely fitted to the body model 204. In addition, the Huygens' surface is chosen so that it smoothly encloses the entire body model. In FIG. 2, only a portion of the Huygens' surface is shown enclosing a portion of the body model 204 for clarity and to illustrate the body model 204. As mentioned, the Huygens' surface will enclose the entire body model. The body model 204 also includes a nerve atlas. At block 106, the Huygens' surface 202 is densely populated with elements that serve as basis functions for the magnetic fields. In one embodiment, the basis elements are small current loops 206, as shown in FIG. 2. The number and size of the loops can be chosen so as to yield a complete basis. In one example, approximately 3000 bases with a few millimeters in diameter may be used to densely populate the Huygens' surface. In other embodiments, other basis elements (other than loops) may be added on the Huygens' surface, for example, electric dipoles. However, current loops (i.e., magnetic dipoles) have been found to account for the vast majority of the EM variability achievable at the kHz frequencies relevant for PNS. At block 108, magnetic field components ($B_x$, $B_y$, $B_z$) are simulated on the boundary of the body model 204 for every Huygens' basis. At block 110, a matrix $B_H$ is created from the simulated magnetic fields induced by each Huygens' basis. The matrix $B_H$ has a size of $b \times n_H$ where b is the number of points on the boundary of the body model and $n_H$ is the number of Huygens' basis functions. The matrix $B_H$ may be simulated, for example, using the fast Biot-Savart formulation, since MRI gradients and other coils relevant for PNS are operated in the low kHz frequency range. In an embodiment, the matrix $B_H$ is pre-computed and only needs to be generated once for each body model.

Figure 3:
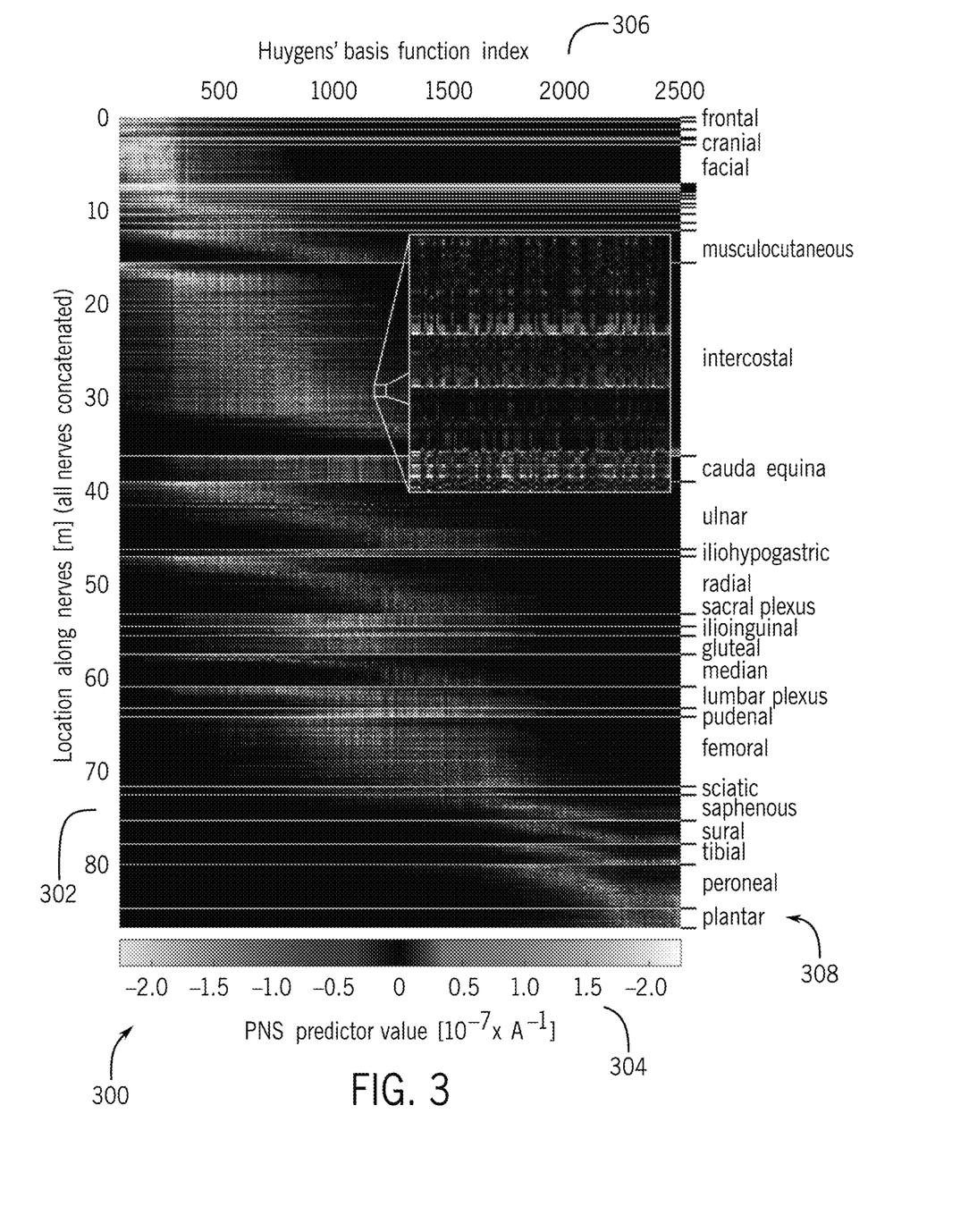
FIG. 3 illustrates an example PNS Huygens' P-matrix in accordance with an embodiment.

At block 112, the electric field that every Huygens' basis function induces in the body model 204 is simulated. Diagram 208 illustrates an example electric field of Huygens' basis. At block 114, a PNS predictor value 212 is extracted along all nerves of the body model's nerve atlas, for example, as illustrated in diagram 210 in FIG. 2. In one embodiment, the PNS predictor (or oracle) values (PNSO) may be determined using:

$$PNSO(r) = \frac{K(D)}{m(D)} * \frac{V(r-L) - 2V(r) + V(r+L)}{L(D)^2}$$

where V(r) is the extracellular potential along the nerve position r, L(D) is the distance between consecutive nodes of Ranvier (which is a function of the axon diameter D), K(D) is a spatial kernel, and m(D) is a calibration factor. At block 112, the PNS Huygens' P-matrix ($P_H$) is created by combining the PNS predictor values induced by all Huygens' bases along all nerve segments. The PNS Huygens' P-matrix is a linear P-matrix. The PNS Huygens' P-matrix ($P_H$) has a size of $p \times n_H$ where p is number of nerve segments in the body model and $n_H$ is the number of basis functions on the Huygens' surface. At block 214, PNS Huygens' P-matrix ($P_H$) and the matrix $B_H$ may be stored in a memory or data storage of, for example, an MRI system (e.g., MRI system 700 discussed below with respect to FIG. 7) or other computer system (e.g., computer system 600 discussed below with respect to FIG. 6). The PNS Huygens' P-matrix ($P_H$) and matrix $B_H$ may be obtained or retrieved from the memory or data storage FIG. 3 illustrates an example PNS Huygens' P-matrix 300 in accordance with an embodiment. The Huygens' basis functions 306 (columns) are ordered from head to feet. In this embodiment, the nerve segments 302 (rows) are clustered into groups of the major anatomical nerves 308 which are also ordered from head to feet. Scale 304 shows the different PNS predictor values indicated in the matrix by shading.

Figure 4:
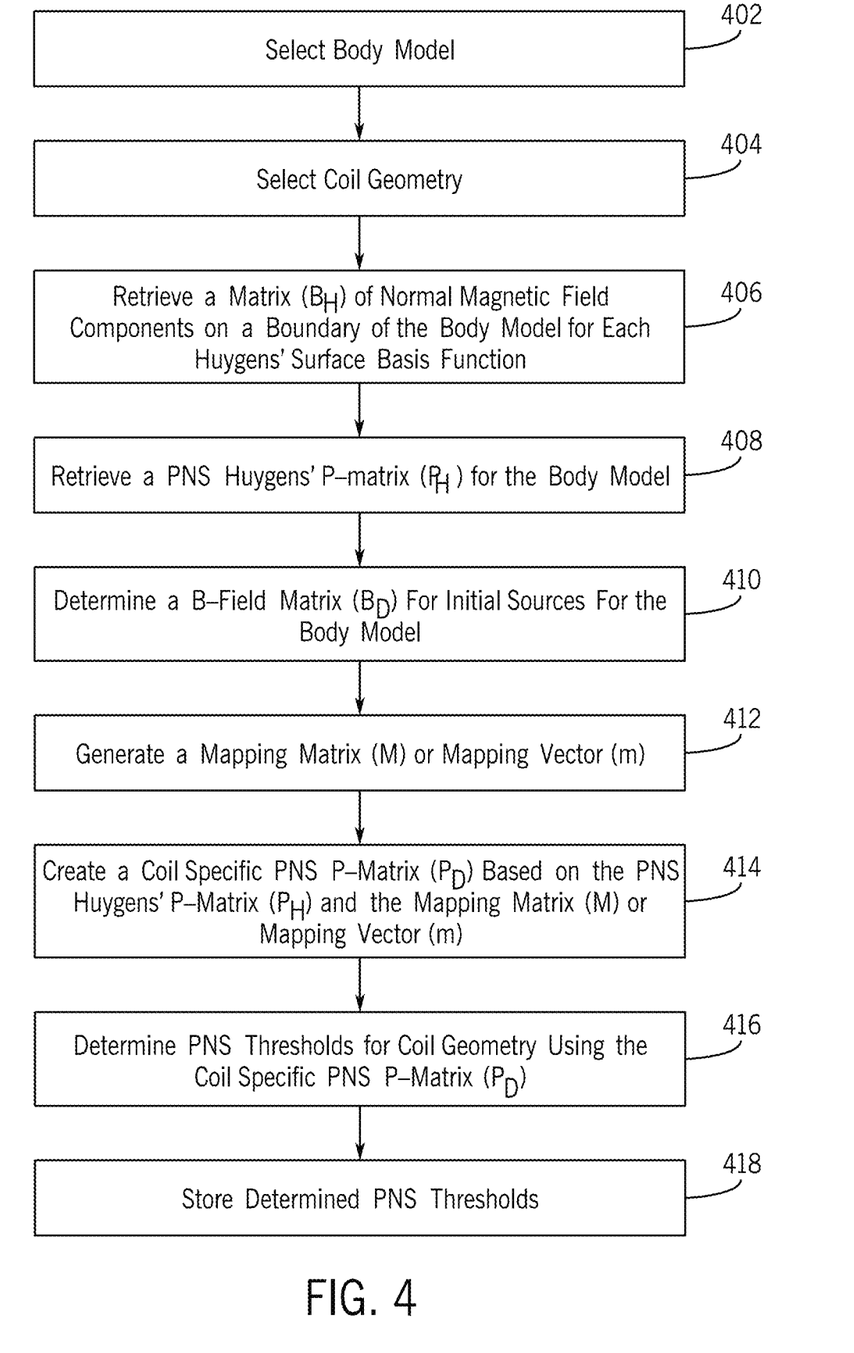
FIG. 4 illustrates a method for assessing peripheral nerve stimulation (PNS) for a coil geometry in accordance with an embodiment.

FIG. 4 illustrates a method for assessing peripheral nerve stimulation (PNS) for a coil geometry in accordance with an embodiment. At block 402, a body model is selected. At block 404, a coil geometry, for example, a coil former shape or coil winding pattern, is selected for PNS assessment. As mentioned above, the coil geometry may be for a device such as a gradient coil or a magneto-stimulation device. In one embodiment, the body model and the coil geometry may be selected by a user via a user input of a computer system. At block 406, a matrix of magnetic field components ($B_H$) on a boundary of a body model is obtained or retrieved. In one embodiment, the matrix $B_H$ may be generated for a set of Huygens' surface bases as described above with respect to FIG. 1. In an embodiment, the matrix $B_H$ may be pre-computed and stored in a memory or data storage. The matrix $B_H$ may be obtained or retrieved from the memory or data storage. At block 408, a PNS Huygens' P-matrix ($P_H$) for the body model may be obtained or retrieved. The PNS Huygens' P-matrix ($P_H$) facilitates the rapid determination or optimization of the response of peripheral nerves to any winding pattern (the sources) located beyond the Huygens' surface. An example method for generating the PNS Huygens' P-matrix ($P_H$) is described above with respect to FIG. 1. While generation of the PNS Huygens' P-matrix is typically slow (approximately one month per body model), the PNS Huygens' P-matrix only needs to be generated once per body model and is fixed for any arrangement of the sources located beyond the Huygens' surface. Accordingly, in an embodiment, the PNS Huygens' P-matrix ($P_H$) may be pre-computed and stored in a memory or data storage The PNS Huygens' P-matrix ($P_H$) may be obtained or retrieved from the memory or data storage.

At block 410, a B-field matrix ($B_D$) is determined for initial sources for the body model. The B-field matrix $B_D$ is determined for the initial sources (located beyond the Huygens' surface) by simulating the magnetic field component on the boundary of the body model for each initial source (similar to the $B_H$ matrix of the Huygens' basis functions). The resulting matrix $B_D$ has a size $b \times n_D$ where b is the number of points on the body model boundary and $n_D$ is the number of sources. The B-field matrix $B_D$ may be stored in memory or data storage of, for example, an MRI system (e.g., MRI system 700 discussed below with respect to FIG. 7) or other computer system (e.g., computer system 600 discussed below with respect to FIG. 6).

Figure 5:
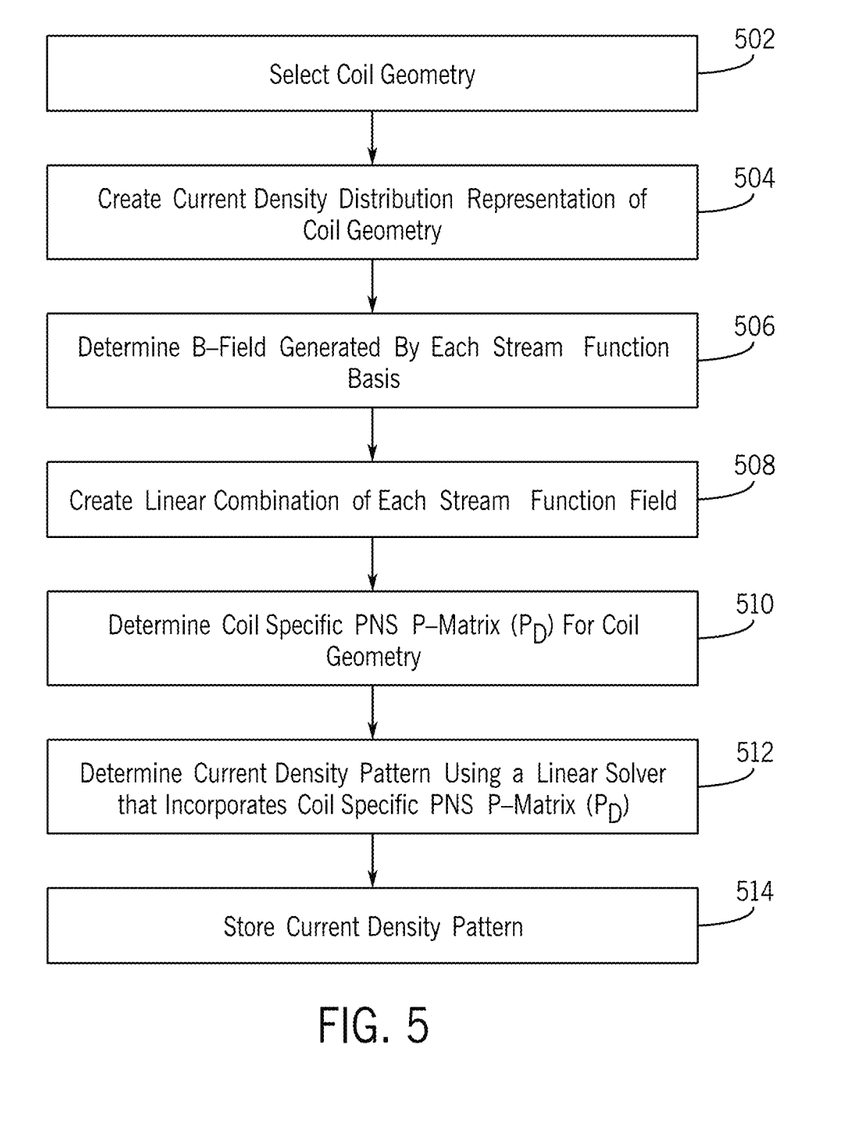
FIG. 5 illustrates a method for gradient coil design and optimization in accordance with an embodiment.

At block 412, a mapping matrix (M) or a mapping vector (m) is generated. In one embodiment, a mapping matrix (M) is generated if the coil specific PNS P-matrix $P_D$ will be used for optimization of a gradient coil and will be directly incorporated into a standard gradient winding optimization approach (e.g., BEM-SF). In an embodiment, the mapping matrix M may be generated by solving a system of linear matrix equations including the matrices $B_H$ and $B_D$ (described above) using Tikhonov regularized pseudo-inverse:

$$M = (B_H^T B_H + \lambda^2 I)^{-1} B_H^T B_D \qquad \text{Eqn. 2}$$

where $B_H$ and $B_D$ are the B-field matrices described above, I denotes the identity matrix, $\lambda$ is the regularization strength and T denotes the transpose of the matrix. The mapping matrix M has a size of $n_H \times n_D$ where $n_H$ is the number of Huygens' basis functions and $n_D$ is the number of basis functions on the design surface or the number of independently driven discrete coils (such as gradient coil axes or coils of a magnetic stimulator device). In other embodiments, other known approaches may be used to generate the mapping matrix M, such as directly solving the linear system for each basis function using linear optimization solvers. In another embodiment, a mapping vector m is generated if the coil specific PNS P-matrix $P_D$ will be used to predict PNS thresholds for a single discrete coil winding (e.g., existing gradient coils). A mapping vector (m) may be used rather than the mapping matrix (M) in this embodiment because the coil corresponds to a single basis element. In this embodiment, the sources are discrete wires instead of stream functions. Generation of the mapping vector (m) may also performed using Eqn 2. The mapping matrix (M) and mapping vector (m) may be stored in memory or data storage of, for example, an MRI system (e.g., MRI system 500 discussed below with respect to FIG. 5) or other computer system (e.g., computer system 400 discussed below with respect to FIG. 4). Advantageously, in one example the generation of mapping matrix M or the mapping vector is very fast (e.g., only a few seconds). The mapping matrix M may be generated very quickly (seconds) because it only involves: 1) calculation of the magnetic field created by the sources beyond the Huygens' surface (which only takes seconds), namely, the matrix $B_D$; and 2) solving a system of linear equations. As mentioned above with respect to block 406, the matrix $B_H$ may be pre-computed for a set of Huygens' surface bases and, for example, retrieved from a memory or storage device.

At block 414, a coil specific PNS P-matrix ($P_D$) may be created using the PNS Huygens' P-matrix ($P_H$) and either the mapping matrix (M) or the mapping vector (m). The coil specific PNS P-matrix is a linear P-matrix. In one embodiment, the coil specific PNS P-matrix $P_D$ may be used for optimization of a gradient coil. In order to translate or map the general PNS Huygens' P-matrix $P_H$ to a coil specific PNS P-matrix $P_D$, a projection operation of the initial sources (located beyond the Huygens' surface) to the Huygens' surface is performed and is expressed mathematically as:

$$P_D = P_H M \qquad \text{Eqn. 3}$$

The coil specific PNS P-matrix $P_D$ assigns a value (a predictor value) to each section of a nerve that inversely scales with the PNS threshold. The PNS threshold may be given by the inverse of the maximum absolute PNS P-matrix $P_D$, namely:

$$\max\{|P_H M|^{-1}\} \qquad \text{Eqn. 4}$$

In another embodiment, the coil specific PNS P-matrix $P_D$ may be used to predict PNS thresholds for single discrete coil winding (e.g., an existing gradient coil). In this embodiment, the projection of the Huygens' $P_H$ matrix is achieved using a mapping vector m. As mentioned, above, a mapping vector (m) may be used in this embodiment rather than a mapping matrix (M), because the coil corresponds to a single basis element. The projection operation may be expressed as:

$$P_D = P_H m \qquad \text{Eqn. 5}$$

As mentioned above, the coil specific PNS P-matrix $P_D$ assigns a value (a predictor value) to each section of a nerve that inversely scales with the PNS threshold. The PNS threshold may be given by the inverse of the maximum absolute PNS P-matrix $P_D$, namely:

$$\max\{|P_H m|^{-1}\} \qquad \text{Eqn. 6}$$

At block 416, PNS thresholds may be determined using the coil specific PNS P-matrix ($P_D$), for example, by determining the inverse of the coil specific PNS matrix PNS predictor values as given by Eqn 4 and 6. A PNS threshold is the smallest stimulating coil current amplitude inducing an action potential (AP). At block 418, the PNS thresholds may be stored in memory or data storage of, for example, an MRI system (e.g., MRI system 700 discussed below with respect to FIG. 7) or other computer system (e.g., computer system 600 discussed below with respect to FIG. 6). In an embodiment, a report may be generated indicating the PNS thresholds (using, for example, a chart, graph or image) and provided to and shown on a display (e.g., display 618 shown in FIG. 6 or display 704, 736 or 744 shown in FIG. 7). The report may also be stored in memory or data storage.

The PNS Huygens' P-matrix ($P_H$) fully describes the body models' electric fields (i.e., the electric fields induced in the body model) and their interaction with the nervous system. The PNS Huygens' P-matrix is defined on the smooth Huygens' surface enclosing the body model. Instead of re-computing electric fields and PNS predictor values for different coil windings or different coil former shapes within numeric coil winding optimization as required by prior PNS predictor tools, the systems and methods described herein facilitate the quick translation or mapping of the PNS Huygens' P-matrix to arbitrary coil former surfaces and coil windings using the mapping matrix or mapping vector. As mentioned, the PNS Huygens' P-matrix approach described herein may be applicable to both discrete coil winding patterns (e.g., existing or hypothetical MRI gradient coils) and continuous current density patterns (i.e., the coil specific PNS P-matrix can be directly incorporated into, for example, the standard BEM-SF approach for numeric gradient winding optimization).

In another embodiment the coil specific PNS P-matrix may be used to rapidly assess PNS (e.g., predict PNS thresholds) for a magneto-stimulation (or magnetic stimulator) device, for example, consisting of an array of magnetic coils, that may be used for therapy and treatment applications. In this embodiment, the coil specific PNS matrix ($P_D$) may be split into two matrices based on the desired nerves to be stimulated. In particular, a matrix $P_{tar}$ may be created from a set of targeted nerves to be stimulated and a matrix $P_{avd}$ may be created from the remaining nerves in the matrix $P_D$ for which stimulation must be avoided. The matrices $P_{tar}$ and $P_{avd}$ may be used to identify a weight vector $x_{opt}$ (denoting electric current or voltages of independently driven coils) that specifies the optimal weighting by which every element of the stimulation device needs to be driven. In other words, the weight vector $x_{opt}$ maximally stimulates given target nerves while sparing all other nerves. In one embodiment, this can be expressed as:

$$x_{opt} = \arg\max_{x} \{\underbrace{\max\{|P_{tar}x|\}}_{\text{Stimulation of target nerves}}\} \qquad \text{Eqn. 7}$$

$$\text{s.t.} \quad \underbrace{\max\{|P_{avd}x|\}}_{\text{Stimulation of non-target nerves}} \leq \varepsilon \text{ and } |x| \leq I_{max} \text{ or } V_{max}$$

where $P_{tar}$ denotes the portion of the PNS matrix for the nerves to be stimulated, $P_{avd}$ denoting the portion of the PNS matrix, for which stimulation must be avoided, and $I_{max}$ and $V_{max}$ denote the maximum current or voltage per independently driven coil used to perform the targeted stimulation.

Figure 6:
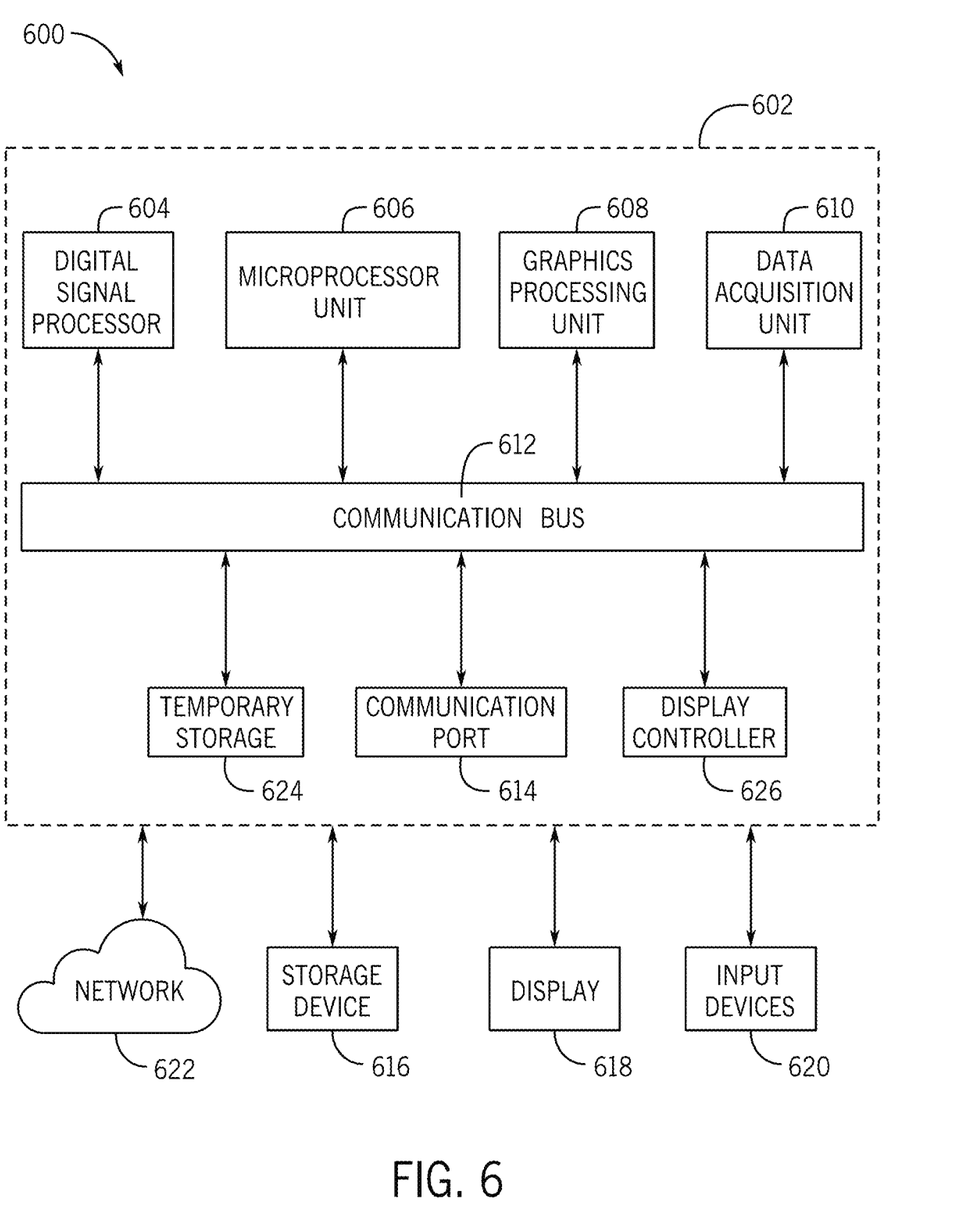
FIG. 6 is a block diagram of an example computer system in accordance with an embodiment.

As mentioned above, in another embodiment, a coil specific PNS P-matrix $P_D$ may be used for optimization of a gradient coil and may be directly incorporated into a BEM-SF gradient winding optimization approach. FIG. 5 illustrates a method for gradient coil design and optimization in accordance with an embodiment. At block 502, a gradient coil geometry (e.g., a coil former shape or winding patterns). In one embodiment, the gradient coil geometry may be selected by a user via a user input of a computer system. At block 504, a current density distribution representation of the gradient coil geometry is created on a coil former mesh (e.g., a cylinder mesh). Every vertex of the mesh carries a discrete current density element called a stream function basis. At block 506, the B-field generated by each stream function basis is determined. For example, the B-field for each stream function basis may be pre-computed. At block 508, a linear combination of each stream function's B-field is created as an expression of the total field. At block 510, a coil specific PNS P-matrix ($P_D$) is determined using, for example, the method described above with respect to FIG. 4. As mentioned above, the coil specific PNS P-matrix is a linear P-matrix. At block 512, a current density pattern (i.e., a set of weighted basis functions) is determined using a linear solver that incorporates the coil specific PNS P-matrix ($P_D$). As mentioned above, the coil specific PNS P-matrix ($P_D$) is incorporated in the optimization process to enforce PNS-optimized coil layouts. In an embodiment, the linear solver determines the current density pattern such that the total field matches the target field. At block 514, the current density pattern may be stored in memory or data storage of, for example, an MRI system (e.g., MRI system 700 discussed below with respect to FIG. 7) or other computer system (e.g., computer system 600 discussed below with respect to FIG. 6). In an embodiment, a report may be generated indicating the current density pattern (using, for example, a chart, graph or image) and provided to and shown on a display (e.g., display 618 shown in FIG. 6 or display 704, 736 or 744 shown in FIG. 7). The report may also be stored in memory or data storage The disclosed systems and methods may be implemented using a computer system. FIG. 6 is a block diagram of an example computer system in accordance with an embodiment. Computer system 600 may be used to implement the methods described herein. In some embodiments, the computer system 600 may be a workstation, a notebook computer, a tablet device, a mobile device, a multimedia device, a network server, a mainframe, one or more controllers, one or more microcontrollers, or any other general-purpose or application-specific computing device. The computer system 600 may operate autonomously or semi-autonomously, or may read executable software instructions from the memory or storage device 616 or a computer-readable medium (e.g., a hard drive, a CD-ROM, flash memory), or may receive instructions via the input device 622 from a user, or any other source logically connected to a computer or device, such as another networked computer or server. Thus, in some embodiments, the computer system 600 can also include any suitable device for reading computer-readable storage media.

Data, such as data acquired with an imaging system (e.g., a CT imaging system, a magnetic resonance imaging (MM) system, etc.) may be provided to the computer system 600 from a data storage device 616, and these data are received in a processing unit 602. In some embodiment, the processing unit 602 includes one or more processors. For example, the processing unit 602 may include one or more of a digital signal processor (DSP) 604, a microprocessor unit (MPU) 606, and a graphics processing unit (GPU) 608. The processing unit 602 also includes a data acquisition unit 610 that is configured to electronically receive data to be processed. The DSP 604, MPU 606, GPU 608, and data acquisition unit 610 are all coupled to a communication bus 612. The communication bus 612 may be, for example, a group of wires, or a hardware used for switching data between the peripherals or between any components in the processing unit 602.

The processing unit 602 may also include a communication port 614 in electronic communication with other devices, which may include a storage device 416, a display 418, and one or more input devices 620. Examples of an input device 620 include, but are not limited to, a keyboard, a mouse, and a touch screen through which a user can provide an input. The storage device 616 may be configured to store data, which may include data such as body models, coil geometries for gradient coils and magneto-stimulation devices, PNS Huygens' P-matrices, coil specific PNS P-matrices, B-field matrices and mapping matrices/vectors whether these data are provided to, or processed by, the processing unit 602. The display 618 may be used to display images and other information, such as magnetic resonance images, patient health data, and so on.

The processing unit 602 can also be in electronic communication with a network 622 to transmit and receive data and other information. The communication port 614 can also be coupled to the processing unit 602 through a switched central resource, for example the communication bus 612. The processing unit can also include temporary storage 624 and a display controller 626. The temporary storage 624 is configured to store temporary information. For example, the temporary storage 624 can be a random access memory.

Figure 7:
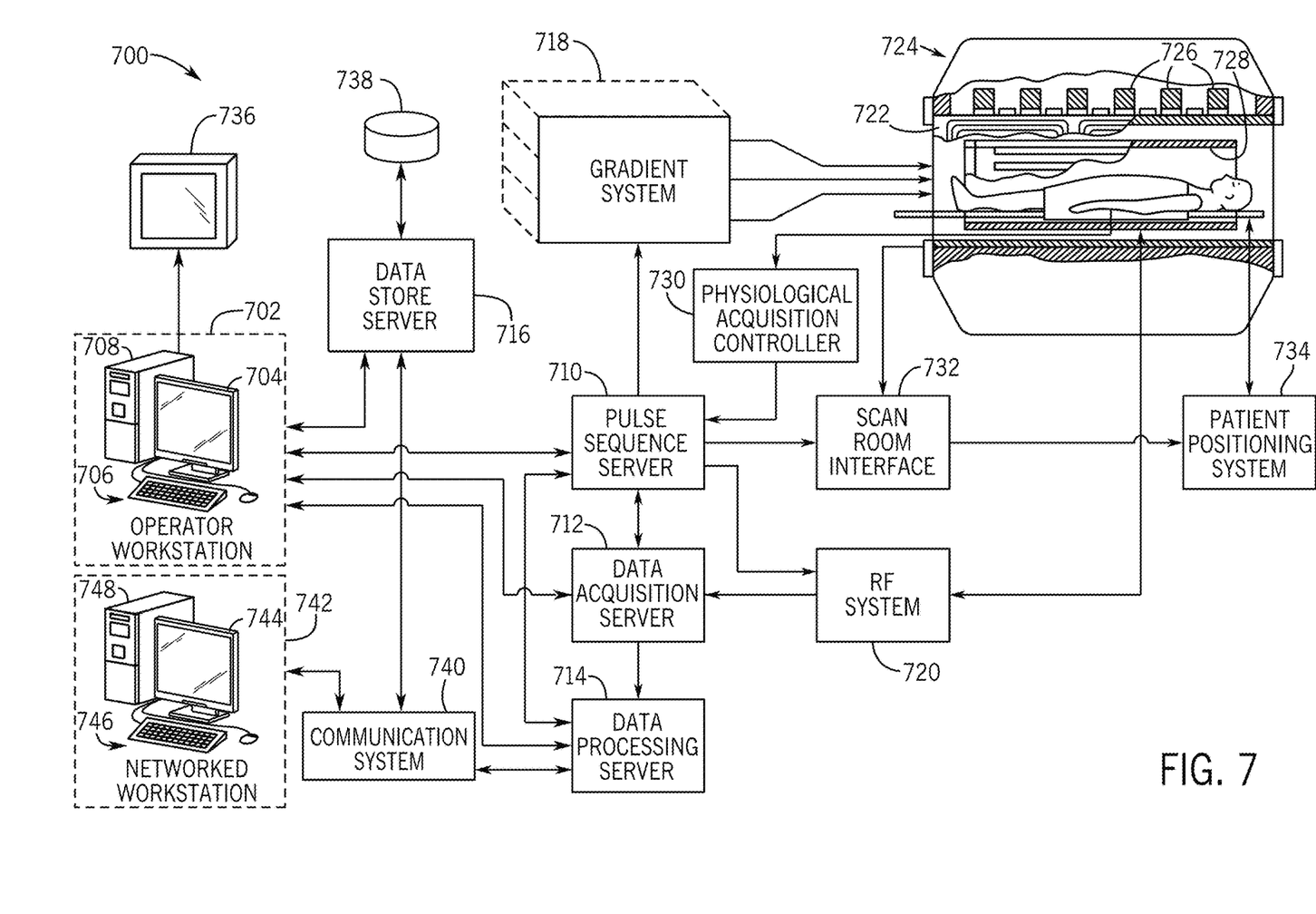
FIG. 7 is a block diagram of an example MRI system for use in accordance with an embodiment.

In the embodiments, the disclosed systems and methods may be implemented using or designed to accompany a magnetic resonance imaging ("MRI") system 100, such as is illustrated in FIG. 7. The MRI system 700 includes an operator workstation 702, which will typically include a display 704, one or more input devices 706 (such as a keyboard and mouse or the like), and a processor 708. The processor 708 may include a commercially available programmable machine running a commercially available operating system. The operator workstation 702 provides the operator interface that enables scan prescriptions to be entered into the MRI system 700. In general, the operator workstation 702 may be coupled to multiple servers, including a pulse sequence server 710; a data acquisition server 712; a data processing server 714; and a data store server 716. The operator workstation 702 and each server 710, 712, 714, and 716 are connected to communicate with each other. For example, the servers 710, 712, 714, and 716 may be connected via a communication system 740, which may include any suitable network connection, whether wired, wireless, or a combination of both. As an example, the communication system 740 may include both proprietary or dedicated networks, as well as open networks, such as the internet.

The pulse sequence server 710 functions in response to instructions downloaded from the operator workstation 702 to operate a gradient system 718 and a radiofrequency ("RF") system 720. Gradient waveforms to perform the prescribed scan are produced and applied to the gradient system 718, which excites gradient coils in an assembly 722 to produce the magnetic field gradients $G_x$, $G_y$, $G_z$ used for position encoding magnetic resonance signals. The gradient coil assembly 722 forms part of a magnet assembly 724 that includes a polarizing magnet 726 and a whole-body RF coil 728.

RF waveforms are applied by the RF system 720 to the RF coil 728, or a separate local coil (not shown in FIG. 7), in order to perform the prescribed magnetic resonance pulse sequence. Responsive magnetic resonance signals detected by the RF coil 728, or a separate local coil, are received by the RF system 720, where they are amplified, demodulated, filtered, and digitized under direction of commands produced by the pulse sequence server 710. The RF system 720 includes an RF transmitter for producing a wide variety of RF pulses used in MM pulse sequences. The RF transmitter is responsive to the scan prescription and direction from the pulse sequence server 710 to produce RF pulses of the desired frequency, phase, and pulse amplitude waveform. The generated RF pulses may be applied to the whole-body RF coil 728 or to one or more local coils or coil arrays.

The RF system 720 also includes one or more RF receiver channels. Each RF receiver channel includes an RF preamplifier that amplifies the magnetic resonance signal received by the coil 728 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M=\sqrt{I2+Q2} \qquad \text{Eqn. 6}$$

and the phase of the received magnetic resonance signal may also be determined according to the following relationship:

$$\varphi = \tan^{-1}\left(\frac{Q}{I}\right) \qquad \text{Eqn. 7}$$

The pulse sequence server 710 also optionally receives patient data from a physiological acquisition controller 730. By way of example, the physiological acquisition controller 730 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 710 to synchronize, or "gate," the performance of the scan with the subject's heart beat or respiration.

The pulse sequence server 710 also connects to a scan room interface circuit 732 that receives signals from various sensors associated with the condition of the patient and the magnet system. It is also through the scan room interface circuit 732 that a patient positioning system 734 receives commands to move the patient to desired positions during the scan.

The digitized magnetic resonance signal samples produced by the RF system 720 are received by the data acquisition server 712. The data acquisition server 712 operates in response to instructions downloaded from the operator workstation 702 to receive the real-time magnetic resonance data and provide buffer storage, such that no data is lost by data overrun. In some scans, the data acquisition server 712 does little more than pass the acquired magnetic resonance data to the data processor server 714. However, in scans that require information derived from acquired magnetic resonance data to control the further performance of the scan, the data acquisition server 712 is programmed to produce such information and convey it to the pulse sequence server 710. For example, during prescans, magnetic resonance data is acquired and used to calibrate the pulse sequence performed by the pulse sequence server 710. As another example, navigator signals may be acquired and used to adjust the operating parameters of the RF system 720 or the gradient system 718, or to control the view order in which k-space is sampled. In still another example, the data acquisition server 712 may also be employed to process magnetic resonance signals used to detect the arrival of a contrast agent in a magnetic resonance angiography ("MRA") scan. By way of example, the data acquisition server 712 acquires magnetic resonance data and processes it in real-time to produce information that is used to control the scan.

The data processing server 714 receives magnetic resonance data from the data acquisition server 712 and processes it in accordance with instructions downloaded from the operator workstation 702. Such processing may, for example, include one or more of the following: reconstructing two-dimensional or three-dimensional images by performing a Fourier transformation of raw k-space data; performing other image reconstruction techniques, such as iterative or back-projection reconstruction techniques; applying filters to raw k-space data or to reconstructed images; generating functional magnetic resonance images; calculating motion or flow images; and so on.

Images reconstructed by the data processing server 714 are conveyed back to the operator workstation 702. Images may be output to operator display 712 or a display 736 that is located near the magnet assembly 724 for use by attending clinician. Batch mode images or selected real time images are stored in a host database on disc storage 738. When such images have been reconstructed and transferred to storage, the data processing server 714 notifies the data store server 716 on the operator workstation 702. The operator workstation 702 may be used by an operator to archive the images, produce films, or send the images via a network to other facilities.

The MRI system 700 may also include one or more networked workstations 742. By way of example, a networked workstation 742 may include a display 744, one or more input devices 746 (such as a keyboard and mouse or the like), and a processor 748. The networked workstation 742 may be located within the same facility as the operator workstation 702, or in a different facility, such as a different healthcare institution or clinic. The networked workstation 742 may include a mobile device, including phones or tablets.

The networked workstation 742, whether within the same facility or in a different facility as the operator workstation 702, may gain remote access to the data processing server 714 or data store server 716 via the communication system 740. Accordingly, multiple networked workstations 742 may have access to the data processing server 714 and the data store server 716. In this manner, magnetic resonance data, reconstructed images, or other data may exchange between the data processing server 714 or the data store server 716 and the networked workstations 742, such that the data or images may be remotely processed by a networked workstation 742. This data may be exchanged in any suitable format, such as in accordance with the transmission control protocol ("TCP"), the internet protocol ("IP"), or other known or suitable protocols.

Computer-executable instructions for assessing peripheral nerve stimulation (PNS) for gradient coils according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access The present invention has been described in terms of one or more preferred embodiments, and it should be appreciated that many equivalents, alternatives, variations, and modifications, aside from those expressly stated, are possible and within the scope of the invention.

The invention claimed is:

1. A method for assessing peripheral nerve stimulation (PNS) for a coil geometry, the method comprising:
retrieving a PNS Huygens' penalty matrix (P-matrix) for a body model, the PNS Huygens' P-matrix defined on a Huygens' surface enclosing the body model;
generating a coil specific PNS P-matrix for the coil geometry based on at least the PNS Huygens' P-matrix for the body model;
determining at least one PNS threshold for the coil geometry based on the coil specific PNS P-matrix;
storing the at least one PNS threshold in a storage device;
determining an adjustment of one or more of a parameter of or position of the coil geometry based on the at least one PNS threshold for the coil geometry; and
adjusting the one or more of a parameter or a position of the coil geometry based on the determined adjustment.

2. The method according to claim 1, wherein the coil geometry is a gradient coil geometry.

3. The method according to claim 1, wherein the coil geometry is a magneto-stimulation device coil geometry.

4. The method according to claim 1, wherein the coil geometry is a coil former shape.

5. The method according to claim 1, wherein the coil geometry is a coil winding pattern.

6. The method according to claim 4, wherein generating the coil specific PNS P-matrix for a coil former shape is further based on a mapping matrix.

7. The method according to claim 6, wherein generating the coil specific PNS P-matrix for a coil former shape is given by:

$$P_D = P_H M$$

where $P_D$ is the coil specific PNS P-matrix for the coil former shape, $P_H$ is the PNS Huygens' P-matrix and M is the mapping matrix.

8. The method according to claim 6, further comprising generating the mapping matrix by solving a set of linear matrix equations.

9. The method according to claim 5, wherein generating the coil specific PNS P-matrix for a coil winding pattern is further based on a mapping vector.

10. The method according to claim 9, wherein generating the coil specific PNS P-matrix for a coil winding pattern is given by:

$$P_D = P_H m$$

where $P_D$ is the coil specific PNS P-matrix for the coil winding pattern, $P_H$ is the PNS Huygens' P-matrix and m is the mapping vector.

11. The method according to claim 10, wherein determining at least one PNS threshold for the gradient coil geometry based on the coil specific PNS P-matrix for the coil winding pattern includes determining an inverse of the maximum absolute coil specific PNS P-matrix as given by:

$$\max\{|P_H m|^{-1}\}$$

12. The method according to claim 1, wherein the Huygens' surface is configured to enclose the body model and maintain a predetermined minimum distance between the Huygens' surface and a boundary of the body model.

13. The method according to claim 1, wherein the coil specific PNS P-matrix for the gradient coil geometry is a linear P-matrix.

14. A magnetic resonance imaging (MRI) system comprising:
a magnet system configured to generate a polarizing magnetic field about at least a portion of a subject;
a magnetic gradient system including a plurality of gradient coils configured to apply at least one gradient field to the polarizing magnetic field;
a radio frequency (RF) system configured to apply an excitation field to the subject and to receive MR data from the subject using a coil array; and
a computer system programmed to:
retrieve a peripheral nerve stimulation (PNS) Huygens' penalty matrix (P-matrix) for a body model, the PNS Huygens' P-matrix defined on a Huygens' surface enclosing the body model;
generate a coil specific PNS P-matrix for a predetermined gradient coil geometry based on at least the PNS Huygens' P-matrix for the body model;
determine at least one PNS threshold for the gradient coil geometry based on the coil specific PNS P-matrix;
store the at least one PNS threshold in a storage device;
determine an adjustment of one or more parameters of the gradient coil geometry based on the at least one PNS threshold for the gradient coil geometry; and
adjust the one or more parameters of the gradient coil geometry based on the determined adjustment.

15. The MRI system according to claim 14, wherein the gradient coil geometry is a coil former shape.

16. The MRI system according to claim 14, wherein the gradient coil geometry is a coil winding pattern.

17. A method for optimizing a design of a gradient coil geometry, the method comprising:
creating a current density distribution of the gradient coil geometry;
determining a B-field generated by each stream function basis associated with the current density distribution;
determining a coil specific peripheral nerve stimulation penalty matrix (PNS P-matrix) for the gradient coil geometry based on at least a PNS Huygens' P-matrix for a body model, the PNS Huygens' P-matrix defined on a Huygens' surface enclosing the body model;
determining a current density pattern using an optimization process including the coil specific PNS P-matrix for the gradient coil geometry;
storing the current density pattern; and
configuring the gradient coil geometry based on the current density pattern.

18. The method according to claim 17, wherein the gradient coil geometry is a coil former shape.

19. The method according to claim 18, wherein determining the coil specific PNS P-matrix for the coil former shape is given by:

$$P_D = P_H M$$

where $P_D$ is the coil specific PNS P-matrix for the coil former shape, $P_H$ is the PNS Huygens' P-matrix and M is a mapping matrix.

20. The method according to claim 17, wherein the Huygens' surface is configured to enclose the body model and maintain a predetermined minimum distance between the Huygens' surface and a boundary of the body model.

* * * * *